US010897922B2

(12) United States Patent
Church et al.

(10) Patent No.: US 10,897,922 B2
(45) Date of Patent: Jan. 26, 2021

(54) COMPOSITION AND METHOD FOR GERMINATIVE COMPOUNDS IN PROBIOTIC FOOD AND BEVERAGE PRODUCTS FOR HUMAN CONSUMPTION

(71) Applicant: NCH Corporation, Irving, TX (US)

(72) Inventors: Jordan E. Church, Dallas, TX (US); Gabriel F. K. Everett, Mansfield, TX (US); Charles J. Greenwald, Irving, TX (US); Lester Levy, Dallas, TX (US); Judy Pruitt, Mesquite, TX (US); Amanda Rosmarin, Lantana, TX (US); Daniel Aberle, Irving, TX (US); George Aboagye, Derby (GB)

(73) Assignee: NCH Corporation, Irving, TX (US)

( * ) Notice: Subject to any disclaimer, the term of this patent is extended or adjusted under 35 U.S.C. 154(b) by 0 days.

(21) Appl. No.: 16/178,905

(22) Filed: Nov. 2, 2018

(65) Prior Publication Data

US 2019/0069587 A1 Mar. 7, 2019

Related U.S. Application Data

(63) Continuation-in-part of application No. 15/479,773, filed on Apr. 5, 2017, now Pat. No. 10,610,552.

(60) Provisional application No. 62/581,324, filed on Nov. 3, 2017, provisional application No. 62/596,424, filed on Dec. 8, 2017, provisional application No. 62/318,587, filed on Apr. 5, 2016.

(51) Int. Cl.
| | |
|---|---|
| *A61K 35/742* | (2015.01) |
| *A23L 33/135* | (2016.01) |
| *A61K 45/06* | (2006.01) |
| *A23L 2/52* | (2006.01) |
| *A61K 38/01* | (2006.01) |
| *A61K 31/198* | (2006.01) |
| *A23L 33/175* | (2016.01) |
| *A23F 3/00* | (2006.01) |
| *A61K 35/00* | (2006.01) |

(52) U.S. Cl.
CPC .............. *A23L 33/135* (2016.08); *A23L 2/52* (2013.01); *A23L 33/175* (2016.08); *A61K 31/198* (2013.01); *A61K 35/742* (2013.01); *A61K 38/011* (2013.01); *A61K 45/06* (2013.01); *A23F 3/00* (2013.01); *A23V 2200/3204* (2013.01); *A61K 2035/115* (2013.01)

(58) Field of Classification Search
None
See application file for complete search history.

(56) References Cited

U.S. PATENT DOCUMENTS

| | | |
|---|---|---|
| 6,327,965 B1 | 12/2001 | Lin Tien |
| 6,461,607 B1 | 10/2002 | Farmer |
| 6,849,256 B1 | 2/2005 | Farmer |
| 7,081,361 B2 | 7/2006 | Pearce, III et al. |
| 7,736,509 B2 | 6/2010 | Kruse |
| 8,192,733 B2 | 6/2012 | Cobb et al. |
| 8,349,337 B1 | 1/2013 | Farmer et al. |
| 9,011,834 B1 | 4/2015 | McKenzie et al. |
| 9,447,376 B2 | 9/2016 | Hashman et al. |
| 9,932,543 B2 | 4/2018 | Hashman et al. |
| 2003/0031659 A1 | 2/2003 | Farmer |
| 2003/0165472 A1 | 9/2003 | McGrath et al. |
| 2003/0228679 A1 | 12/2003 | Smith et al. |
| 2005/0255092 A1 | 11/2005 | Rehberger et al. |
| 2008/0241226 A1 | 10/2008 | Abeln et al. |
| 2009/0041898 A1 | 2/2009 | Garbolino et al. |
| 2009/0186057 A1 | 7/2009 | Farmer et al. |
| 2009/0232941 A1 | 9/2009 | Farmer |
| 2011/0230345 A1 | 9/2011 | Snyder et al. |
| 2011/0256216 A1 | 10/2011 | Lefkowitz |
| 2012/0034344 A1 | 2/2012 | Menon |
| 2012/0052152 A1 | 3/2012 | Armentrout |
| 2012/0100094 A1 | 4/2012 | Reuter et al. |
| 2013/0092087 A1 | 4/2013 | Bachman et al. |
| 2013/0171204 A1 | 7/2013 | DuBourdieu |

(Continued)

FOREIGN PATENT DOCUMENTS

| | | |
|---|---|---|
| CN | 1528681 | 9/2004 |
| EP | 0826311 | 3/1998 |

(Continued)

OTHER PUBLICATIONS

Busta, F.F. and Ordal, Z.J., Use of Calcium Dipicolinate for Enumeration of Total Viable Endospore Populations without Heat Activation, Applied Microbiology, Mar. 1964, p. 106-110, vol. 12, No. 2, American Society for Microbiology.

Carrillo-Martinez, Yarery and Setlow, Peter, Properties of Bacillus subtilis Small, Acid-Soluble Spore Proteins with Changes in the Sequence Recognized by Their Specific Protease, Journal of Bacteriology, Sep. 1994, p. 5357-5363, vol. 176, No. 17, American Society for Microbiology.

(Continued)

*Primary Examiner* — Jennifer E Graser
(74) *Attorney, Agent, or Firm* — Scheef & Stone, LLP; Robin L. Barnes

(57) ABSTRACT

A composition and method for activating probiotic spores in food and beverage products, such as steeped teas, coffee, soups, and sauces. A nutrient-germinant composition comprises one or more L-amino acids, optionally one or more buffers to maintain the pH of the composition when added to water in a range of around 6-8, optionally D-glucose, D-fructose, or both D-glucose and D-fructose, and optionally, an osmoprotectant. The nutrient-germinant composition, one or more species of *Bacillus* spores, and a food or beverage product may be pre-mixed in any combination. Water is added to the mixture and heated to a temperature range of 42 to 100° C. to germinate the probiotic spores prior to being consumed.

19 Claims, 5 Drawing Sheets

(56) References Cited

U.S. PATENT DOCUMENTS

| | | |
|---|---|---|
| 2014/0295482 A1 | 10/2014 | Lyte |
| 2016/0362654 A1 | 12/2016 | Hashman et al. |
| 2017/0281696 A1* | 10/2017 | Everett ............... A61K 35/742 |

FOREIGN PATENT DOCUMENTS

| | | |
|---|---|---|
| WO | WO1999053 10 | 2/1999 |
| WO | WO2004024865 | 3/2004 |
| WO | WO2009126473 | 10/2009 |
| WO | WO2010045541 | 4/2010 |
| WO | WO2010066012 | 6/2010 |
| WO | WO2010079104 | 7/2010 |
| WO | WO2012079973 | 6/2012 |
| WO | WO2014083177 | 6/2014 |
| WO | WO2014193746 | 12/2014 |
| WO | WO2016044661 | 3/2016 |
| WO | WO2017117089 | 7/2017 |

OTHER PUBLICATIONS

Kleijn, Roelco; Buescher, Joerg M.; Le Chat, Ludovic; Jules, Matthieu; Aymerich, Stephane; and Sauer, Uwe, Metabolic Fluxes during Strong Carbon Catabolite Repression by Malate in Bacillus subtilis, Journal of Biological Chemistry, Jan. 15, 2010, p. 1587-1596, vol. 285, No. 3, The American Society for Biochemistry and Molecular Biology, Inc.

Kong, Lingbo; Zhang, Pengfei; Wang, Guiwen; Yu, Jing; Setlow, Peter; and Li, Yong-Qing, Charactization of bacterial spore germination using phase-contrast and fluorescence microscopy, Raman spectroscopy and optical tweezers, Nature Protocols, Mar. 2011, p. 625-639, vol. 6, No. 5.

Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.

Martin, J. H. and Harper, W. J., Germination Response of Bacillus Licheniformis Spores to Amino Acids, Department of Dairy Technology, Journal of Dairy Science, Jul. 1963, p. 663-667.

Segev, Einat; Rosenberg, Alex; Mamou, Gideon; Sinai, Lior; and Ben-Yehuda, Sigal, Molecular Kinetics of Reviving Bacterial Spores, Journal of Bacteriology, May 2013, p. 1875-1882, vol. 195, No. 9.

Setlow, Peter, Summer Meeting 2013—when the sleepers wake: the germination of spores of Bacillus species, Journal of Applied Microbiology, Sep. 2013, p. 1251-1268.

Sinai, Lior; Rosenberg, Alex; Smith, Yoav; Segev, Einat; and Ben-Yehuda, Sigal, The Molecular Timeline of a Reviving Bacterial Spore, Molecular Cell, Feb. 2015, p. 695-707.

Yasuda, Yoko and Tochikubo, Kunio, Relation between D-Glucose and L- and D-Alanine in the Initiation of Germination of Bacillus subtilis Spore, Microbio. Immunol. Oct. 1983, p. 197-207, vol. 28. No. 2.

Yi, Xuan and Setlow, Peter, Studies of the Commitment Step in the Germination of Spores of Bacillus Species, Journal of Bacteriology, Jul. 2010, p. 3424-3433, vol. 192, No. 13.

Zhang, Pengfei; Setlow, Peter; and Li, Yongqing, Characterization of single heat-activated Bacillus spores using laser tweezers Raman spectroscopy, Optics Express, Sep. 2009, p. 16480-16491, vol. 17, No. 19.

Cutting, Simon M., Bacillus probiotics, Food Microbiology, 28 (2011), pp. 214-220, www.elsevier.com/locate/fm.

Curran et al., Heat Activation Inducing Germination in the Spores of Thermotolerant and Thermophilic Aerobic Bacteria, Journal of Bacteriology; Apr. 1945; vol. 49, No. 4, pp. 335-346.

Sigmaaldrich.com, Buffer Reference Center, Webpage [online]; Apr. 30, 2015 [date verified by web.archive.org; retrieved on Jun. 2, 2017]. Retrieved from the Internet: URL: www.sigmaaldrich.com/life-science/core-bioreagents/biological-buffers/learning-center/buffer-reference-center.

Stewart et al., Commitment of bacterial spores to germinate: A measure of the trigger reaction. Biochemical Journal. Jul. 15, 1981, vol. 198, No. 1; pp. 101-106.

Boukarim et al., Preservatives in Liquid Pharmaceutical Preparations; The Journal of Applied Research; published 2009 (month unknown); vol. 9, No. 1-2; pp. 14-17.

Nagler, et al., High Salinity Alters the Germination Behavior of Bacillus subtilis Spores with Nutrient and Nonnutrient Germinants. Applied and Environmental Microbiology. Feb. 2014, vol. 80, No. 4; pp. 1314-1321.

Gurung, et al. A Broader View: Microbial Enzymes and Their Relevance in Industries, Medicine, and Beyond, Biomed Research International, vol. 2013, Article ID 329121, 18 Pages.

Yazdi et al, Characterization and cloning of the gerC locus of Bacilllus subtilis 168, Journal of General Microbiology (1990), 136, 1335-1342.

Chedia, Aquadhi et al., Optimization of nutrient-induced germination of Bacillus sporothermodurans spores using response surface methodology, Food Microbiology, Academic Press Ltd, V. 36, N. 2, Jul. 8, 2013, pp. 320-326.

Ramirez-Peralta, Arturo et al, Effects of 1-16 sporulation conditions on the germination and germination protein levels of Bacillus subtilis spores, Applied and Environmental Microbiology Apr. 2012, V. 78, N. Apr. 8, 2012, pp. 2689-2697.

Wang, Shiwei et al, Slow Leakage of Ca-Dipicolinic Acid from Individual Bacillus Spores during Initiation of Spore Germination, Journal of Bacteriology, V. 197, N. 6, Mar. 2015, pp. 1095-1103.

Luu, Stephanie, et al., The Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.

Katsutoshi et al., Effect of spore-bearing lactic acid-forming bacteria (Bacillus coagulans SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp. 4-13.

Yeo et al., Antihypertensive Properties of Plant-Based Prebiotics. Int. J. Mol. Sci. 2009, 10, 3517-3530.

Casula, G and S. Cutting. 2002. Bacillus Probiotics: Spore Germination in the Gastrointestinal Tract. American Society for Microbiology. vol. 68, No. 5: 2344-2352.

Wikipedia, "Sodium chloride", Nov. 1, 2017, retrieved on Apr. 5, 2019 from https://en.wikipedia.org/w/index.php?title=Sodium_chloride&oldid=808219406, pp. 1-9.

EcoBionics Biological System Data Sheet, believed to be published at least as early as 2016 (relates to Bioamp).

Waites, The Effect of pH, Germinants and Temperature on the Germination of Spores of Clostridium bifermentans, Journal of General Microbiology, 1974, 80, 253-258 (Year: 1974).

Nguyen, Bacillus subtilis spores expressing the VP28 antigen; a potential oral treatment to protect Litopenaeus vannamei against white spot syndrome, FEMS Microbiilogy Letters Sep. 1, 2014 (Sep. 1, 2014), vol. 358, pp. 202-208, p. 203.

Shearer et al., Bacterial Spore Inhibition and Inactivation in Foods by Pressure, Chemical Preservatives, and Mild Heat, Journal of Food Protection, Nov. 2000, vol. 63, pp. 1503-1510, p. 1504-1505.

Setlow, Germination of Spores of Bacillus Species, What We Know and Do Not Know, Journal of Bacteriologoy, Apr. 2014, vol. 196, pp. 1297-1305, p. 1298.

* cited by examiner

COMPOSITION AND METHOD FOR GERMINATIVE COMPOUNDS IN PROBIOTIC FOOD AND BEVERAGE PRODUCTS FOR HUMAN CONSUMPTION

CROSS REFERENCE TO RELATED APPLICATION

This application claims the benefit of U.S. Provisional Patent Application No. 62/581,324 filed on Nov. 3, 2017. This application also claims the benefit of U.S. Provisional Patent Application No. 62/596,424 filed on Dec. 8, 2017. This application is also a continuation-in-part of U.S. application Ser. No. 15/479,773 filed on Apr. 5, 2017, now U.S. Pat. No. 10,610,552, which claims the benefit of U.S. Provisional Patent Application No. 62/318,587, filed Apr. 5, 2016.

BACKGROUND

Spore germination is a multistep, causative process wherein spores effectively wake-up or are revived from a dormant state to a vegetative growth state. The first step is one by which spores are activated and are induced to germinate, typically by an environmental signal called a germinant. This signal can be a nutrient such as an L-amino acid. Nutrient germinants bind to receptors in the inner-membrane of the spore to initiate germination. Additionally, sugars have been shown to increase the binding affinity of L-amino acids for their cognate receptors.

The germinant signal then initiates a cascade that causes the release of Dipicolinic Acid (DPA), which is stored in a 1:1 ratio with $Ca^{2+}$ (CaDPA) in the core of the spore. The release of CaDPA is a fast process and is typically >90% complete in 2 min. CaDPA release represents a point of no return for spores in which they are committed to the germination process. Those knowledgeable in the art refer to this step as the "commitment" step.

After CaDPA release, the spore is partially hydrated and the core pH rises to approx. 8.0. The core of the spore then expands and the cortex (composed mostly of peptidoglycan) is degraded by core lytic enzymes. The spore absorbs water and consequently loses its refractivity. This loss of refractivity towards the end of the germination process allows spore germination to be monitored via phase-contrast microscopy.

The second phase of germination is an outgrowth step in which the spore's metabolic, biosynthetic, and DNA replication/repair pathways initiate. The outgrowth period has several phases. The first is known as a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation. For instance, the preferred carbon source of several Bacillus species (including subtilis) is malate and Bacillus spores typically contain a large pool of malate that is used during the revival process. Interestingly, deletion mutants that cannot utilize the malate pool display an extended ripening period compared to wild-type spores indicating that the spore malate pool is sufficient to energize the initial outgrowth process. Additionally, spores store small, acid-soluble proteins that are degraded within the first several minutes of revival that serve as an immediate source of amino acids for protein synthesis. After the outgrowth step, spore revival is complete and cells are considered to be vegetatively growing.

It is known that spores can be induced to germinate via heat-activation. Spores of various Bacillus species have been heat-activated at strain-specific temperatures. For example, B. subtilis spores have been heat-activated at 75° C. for 30 minutes while B. licheniformis spores have been heat-activated at 65° C. for 20 minutes. The heat-activation has been shown to cause a transient, reversible unfolding of spore coat proteins. Heat-activated spores can then be germinated for additional time in germination buffers containing nutrient germinants, such as L-alanine. If no nutrient germinant is present, however, spores will return to their pre-heated, non-germinated state.

It is also known that germination can occur at ambient temperatures (near typical room temperature) without heat-activation and with a germination buffer containing nutrients, but the process usually takes longer than with heat-activation. For example, B. licheniformis and B. subtilis spores will germinate at 35° C. or 37° C., respectively, but it takes a longer period of time (e.g. 2 hours) in a germination buffer containing nutrient germinants. Additionally, non-heat-activated spores of B. subtilis have been known to have been germinated in non-nutrient germinant conditions (e.g. $CaCl_2+Na_2DPA$) for an extended period of time.

It is also known to combine the use of heat activation and a nutrient germinant to germinate spores in a two-step process in laboratory settings. The spores are first heat activated by incubating for a period of time (e.g. 30 minutes) at a temperature in the range of 65-75° C. (this specific temperature is species dependent). Then, the spores are transferred into a buffer solution that contains a nutrient germinant, such as L-alanine. It is also known to grow bacteria in a growth chamber located near a use site by feeding pelletized nutrient material (containing sugar, yeast extract, and other nutrients that are not direct spore germinants), bacteria starter, and water into a growth chamber at a controlled temperature range of 16-40° C., and more preferably between 29-32° C., for a growth period of around 24 hours as disclosed in U.S. Pat. No. 7,081,361.

Additionally, recent scientific advances have shed light on the significance of the relationship between human gut bacteria (the microbiome) and general health. The human microbiome is a product of our genetics, our diets, and our environment. Probiotics may be used to alter the human microbiome. Probiotics for human consumption are available as capsules and as food products (e.g. yogurt, beverages, etc.). Although there are examples of probiotic tea on the market, there are none that include an activating component to germinate probiotic spores for improved efficacy. Here, an invention is described that includes the provision of activating compounds with Bacillus bacterial spores for human probiotic consumption in tea, soups, gravies, sauces, hot chocolate, and other food and beverage products, particularly heated liquids and fluids. There is a need for a rapid spore incubation and activation method that will allow generation of active Bacillus species in a single step at a point-of-use location where the bacteria will be distributed to a consumer/user, for example, in the way of a probiotic for use in human (preferably in a probiotic food or beverage product), animal or plant consumption or directly into a water treatment facility or a drain line. Accordingly, this invention describes a simple method for spore germination using a nutrient germinant concentrate simultaneously with heat incubation in a single step.

BRIEF DESCRIPTION OF THE FIGURES

The system and method of the invention are further described and explained in relation to the following drawing wherein.

DETAILED DESCRIPTION

Figure 1:
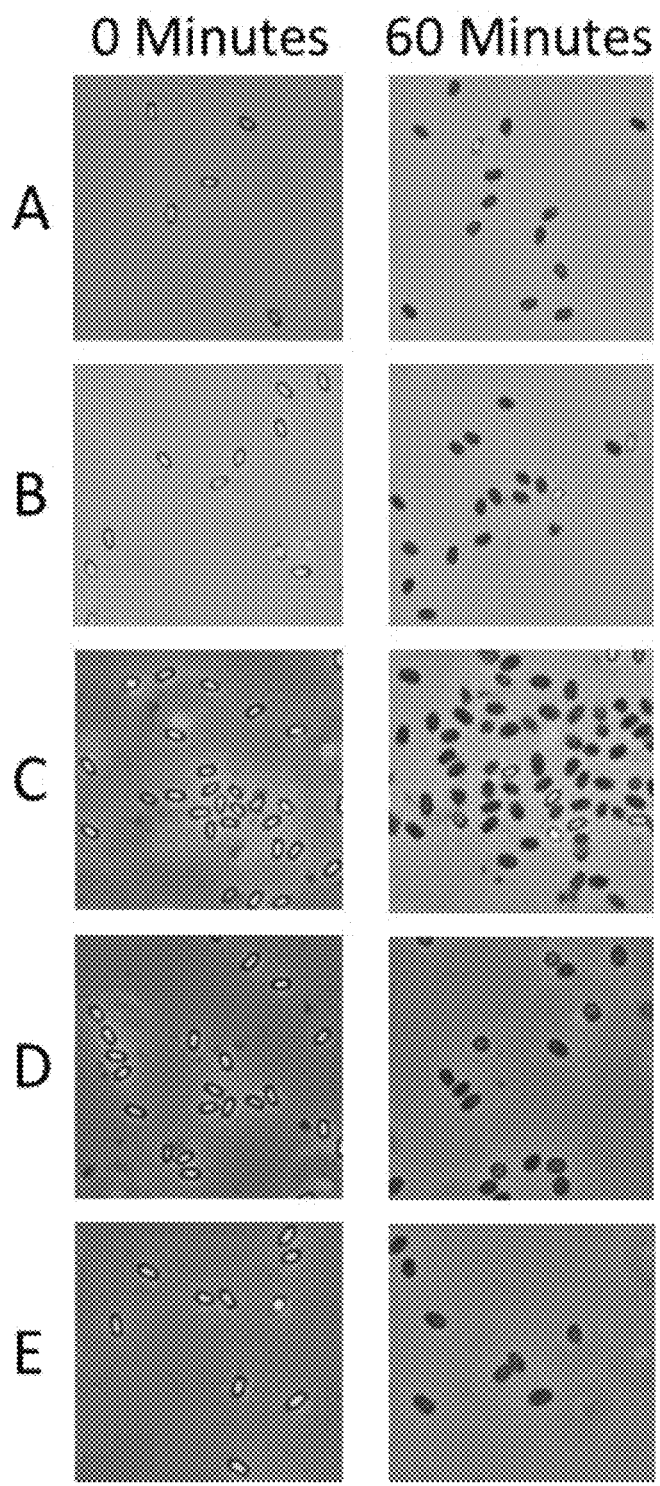
FIG. 1 shows photographs of *Bacillus* species in a nutrient germinant composition according to a preferred embodiment at time zero (when hot water is initially added) and after steeping in hot water for 60 minutes at various temperatures according to preferred methods of the invention, the darker spots indicate germinated bacteria and the lighter/brighter spot indicate non-germinated spores.

Recent scientific advances have shed light on the significance of the relationship between human gut bacteria (the microbiome) and overall health. The human microbiome is a product of our genetics, our diets, and our environment. Probiotics may be used to alter the human microbiome in order to regulate the digestive system and bolster the immune system. Generally, probiotics are non-pathogenic bacteria that may include species of lactic acid bacteria (*Lactobacillus*), *Bifidobacterium*, and *Propionibacterium*. Species of *Bacillus* are also common as probiotics. Probiotics have been widely used in animals as an alternative to hormones and antibiotics, in plants to enhance certain growth characteristics, and in humans as a digestive supplement. Probiotics for human consumption are available as capsules and as food products (e.g. yogurt, juice, etc.). Probiotics delivered in tea are also on the market. Probiotic tea products contain probiotic bacteria packaged with tea in a porous bag. Tea bags are steeped for a period of time in hot water and are consumed. Alternatively, Kombucha tea is a type of probiotic drink in which a symbiotic culture of bacteria and yeast (SCOBY) is added to tea containing sugar. The SCOBY then acts to ferment the sugar in the tea to produce vitamins and acids. In this case, the sugar acts as a substrate and the drink does not contain amino acids that are known to activate bacteria.

In the case of *Bacillus* species as probiotics (e.g. *B. coagulans*), the bacteria are supplied as spores. Spores represent a unique life stage of specific species of bacteria in that these species have the ability to transition into a dormant spore stage if environmental conditions are unfavorable. Spores are naturally dehydrated, are stable for extended periods of time, and are resistant to environmental stresses (e.g. heat, salt, pH, etc.). In the case of *Bacillus* spores in tea products, the spores are preferably more resistant to the high temperatures of steeping water.

In order for spores to return to a live, vegitatively growing state, they must first germinate. Spore germination is a multistep process in which spores are revived from the dormant state. The first step is one by which spores are activated and are induced to germinate, typically by an environmental signal called a germinant. This signal can be a nutrient such as an L-amino acid, potassium ions (e.g. KCl), and/or natural osmoprotectant compounds (e.g. ectoine). Nutrient germinants bind to receptors in the inner-membrane of the spore to initiate germination. Additionally, sugars have been shown to increase the binding affinity of L-amino acids for their cognate receptors.

The germinant signal initiates an irreversible cascade of events, also known as commitment. Commitment is fast and is typically >90% complete in 2 minutes. As germination progresses, the spore rapidly takes on water. As the spore absorbs water it consequently loses its refractivity. This loss of refractivity towards the end of the first phase in the germination process allows spore germination to be observed via phase-contrast microscopy. The initial phase is typically complete within 30 to 60 minutes depending on the temperature. The second phase of germination is an outgrowth step in which the spore's metabolic, biosynthetic, and DNA replication/repair pathways initiate. The outgrowth period includes a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation.

It is known that spores can be induced to germinate via heat-activation. Spores of various *Bacillus* species have been heat-activated at strain specific temperatures (e.g. *B. subtilis* spores can be heat-activated at 75° C. for 30 minutes while *B. licheniformis* spores can be heat-activated at 65° C. for 20 minutes). The heat-activation is believed to cause a transient, reversible unfolding of spore proteins. If the spore proteins are not presented with a nutrient germinant, such as L-alanine, they will refold and effectively reverse the germination process.

The present invention describes a composition and method for activating probiotic spores in food and beverage products, such as steeped teas, soups, gravies, sauces, hot chocolate, coffee, and other products, particularly heated liquids and fluids. The method includes the provision of nutrient germinants with *Bacillus* spores that will be heat activated and subsequently germinated with nutrient germinants while the food or beverage product is being heated, such as while tea is steeping in hot water. According to one preferred embodiment, the two probiotic components (bacterial spores and nutrient germinants) may be provided as dry components in an automatic coffee maker pod (e.g. Keurig®, Nespresso®, Tassimo®, etc.) containing tea or another food or beverage product. According to another preferred embodiment, the ingredients may be provided as mixed ingredients (nutrient germinant composition and spores) in a single serve packet to be added to tea or another food or beverage product, mixed components (nutrient germinant composition and spores) in a single bag containing tea or another food or beverage product, or as separated components in separate tea bags (e.g. two bags containing any combination of the nutrient germinant composition, spores, and tea) or other container for other food or beverage products. According to one preferred embodiment, spores can be heat-activated in the presence of nutrient germinants in a method that is described in U.S. patent application Ser. No. 15/479,773, published as U.S. 2017/0281696, which is incorporated herein by reference.

Nutrient Compositions

Described herein are preferred embodiments of nutrient compositions that may contain one or more L-amino acids, D-glucose, D-fructose, a biological buffer, a potassium ion source, and/or a natural osmoprotectant. All components in the nutrient formulation must be Generally Regarded as Safe (GRAS) for human consumption by the United States Food and Drug Administration. At the time of this writing, most, although not all, of the components described herein have been deemed GRAS.

According to one preferred embodiment, the nutrient germinant composition can include one or more L-amino acids. Preferred L-amino acid(s) included in the nutrient formulation are L-alanine, L-asparagine, L-valine, and/or L-cysteine. The choice of L-amino acids is determined by the species of *Bacillus* used in the probiotic formulation. The L-amino acids can be provided in the form of any suitable source, such as their pure forms and/or a hydrolysate of soy protein.

According to another preferred embodiment, the nutrient germinant composition can optionally contain an amount of D-glucose and/or D-fructose. The choice of sugar is determined by the species of *Bacillus* used in the probiotic formulation.

According to another preferred embodiment, the nutrient germinant composition can optionally contain one or more sources of potassium ions. Preferably, KCl can be included as a source of potassium ions in the nutrient formulation. The inclusion of potassium ions is determined by the species of *Bacillus* used in the probiotic formulation.

According to another preferred embodiment, the nutrient germinant composition can optionally contain one or more biological buffers. The biologic buffer is a buffer that can buffer the nutrient formulation and/or nutrient-spore formulation, to maintain the formulation at the proper pH for spore germination (about pH 6-8). Preferred biologic buffers include, but are not limited to, a phosphate buffer or a HEPES sodium salt. According to another preferred embodiment, monosodium phosphate and disodium phosphate, preferably used together, can be included in the nutrient formulation as buffers. According to another preferred embodiment, a HEPES buffer may be used.

According to another preferred embodiment, the nutrient solution can optionally contain an osmoprotectant compound. Preferably, ectoine, a natural osmoprotectant produced by some species of bacteria, may be included. The inclusion of an osmoprotectant is determined by the species of *Bacillus* used in the probiotic formulation.

According to another preferred embodiment, the nutrient composition comprises one or more industrial preservatives and/or germination inhibitors, such as a combination of propylparaben and methylparaben or other GRAS (Generally Regarded As Safe) preservatives, NaCl and/or D-alanine. According to another preferred embodiment, the nutrient composition is any one of the nutrient compositions described in U.S. patent application Ser. No. 15/479,773, published as U.S. 2017/0281696, incorporated herein by reference.

A nutrient-germinant composition according to one preferred embodiment of the invention comprises one or a combination of many L-amino acids, optionally D-glucose (which increases the binding affinity of L-amino acids for their cognate receptors in the spore coat), and a neutral buffer such as a phosphate buffer, and an industrial preservative, such as the commercially available Kathon/Lingaurd CG (which has active ingredients comprising methyl chloro isothiazolinone and methyl isothiazolinone). A nutrient-germinant composition according to another preferred embodiment of the invention comprises one or a combination of two or more L-amino acids, optionally D-glucose (which increases the binding affinity of L-amino acids for their cognate receptors in the spore coat), HEPES sodium salt (a biological buffer to provide the proper pH for spore germination), and an industrial preservative, such as a combination of propylparaben and methylparaben or other GRAS (Generally Regarded As Safe) preservatives. According to another preferred embodiment, the composition also comprises a source of potassium ions, such as potassium chloride or monopotassium phosphate or dipotassium phosphate. According to another preferred embodiment, the composition includes both D-glucose and D-fructose.

According to another preferred embodiment, the composition also comprises spores of one or more *Bacillus* species and includes a germination inhibitor, such as NaCl, industrial preservatives, or D-alanine, in combination with any of the previously described composition ingredients. The germination inhibitor prevents the spores from germinating prematurely in the nutrient-germinant composition. The germination inhibitor may include chemicals that prevent spore germination such as NaCl, industrial preservatives, or D-alanine. Alternatively, bacterial spores may be separately provided and added to a nutrient-germinant composition according to the invention at the point-of-use and incubation.

According to another preferred embodiment, a nutrient germinant composition according to the invention is in concentrated form and is diluted to 0.01% to 10% strength in water or another diluent at the point-of-use. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

In another preferred embodiment, the present invention comprises a method of germinating spores of *Bacillus* species using a nutrient germinant composition at an elevated temperature; preferably in a range of 35-60° C., more preferably in the range of 38-50° C., and most preferably in the range of 41° C. to 44° C. for a period of time (an incubation period). The incubation period preferably ranges from 2-60 minutes, depending on the application. Most preferably, a nutrient-germinant composition in concentrated form according to a preferred composition of the invention is used in the incubation methods of the invention, but other nutrient-germinant compositions may also be used. Preferably, the incubation method is carried out at or near the point-of-use—the site or near the site where the germinated spores will be used (such as near animal feeding, watering, or bedding sites) or consumed and further comprises dispensing the germinated spores to the point-of-use/consumption. Preferred methods according to the invention may be carried out in any incubation device that has a reservoir capable of holding a volume of spores, liquid (typically water), nutrient-germinant composition and that is capable of heating the mixture during an incubation period. Most preferably, the methods are carried out in a device that is also capable of mixing those ingredients, automatically shutting-off heating at the end of the incubation period, and automatically dispensing a probiotic or treatment solution comprising the spores to a point-of-use/consumption. Preferred methods may also be carried out as a batch process or as a continuous process. Any variety of spore forms, such as dried powder form, a liquid suspension, or a reconstituted aqueous mixture, may be used with the method of the invention.

The preferred embodiments of the invention have broad utility and application and will allow for rapid germination of spores of *Bacillus* species at a point-of-use. The preferred embodiments are particularly useful in preparing spores for use as a probiotic, for feeding to animals for example, and for providing bacteria to treat wastewater systems or provide drain maintenance.

According to yet another preferred embodiment, a nutrient composition may contain ingredients in one or more of the above-reference categories of ingredients and may contain one or more ingredients from within those categories.

Spore Formulations

Preferred embodiments of spore formulations include one or more *Bacillus* species of spores, including but not limited to, *Bacillus licheniformis, Bacillus subtillis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex, Bacillus sphaericus, Bacillus sonorensis, Bacillus, horneckiae, Bacillus axarquiensis, Bacillus mucilaginosus, Bacillus olivae*, and any combinations thereof. All strains in the probiotic formulation must be Generally Regarded as Safe (GRAS) for human consumption by the United States Food and Drug Administration. At the time of filing this application, several, although not all, of the above mentioned strains have been deemed GRAS. Any *Bacillus* species subsequently determined to be GRAS are included here as suitable for use with embodiments of the invention.

Preferred spore formulations can contain 1-20 or more species of *Bacillus* spores. According to one preferred embodiment, a spore formulation can contain 3 strains of *Bacillus* bacteria. According to another preferred embodiment, 2 strains of the *Bacillus* bacteria can each be a different strain of the species *Bacillus licheniformis* and the third strain is a species of *Bacillus subtilis*. According to another preferred embodiment, about 80% of the formulation can be *Bacillus licheniformis* (40% of each strain) and 20% of the spores in the spore formulation can be is *Bacillus subtilis*. According to another preferred embodiment, the spores of the strain(s) included in the spore formulation can be mixed with water or other suitable carrier and/or organic salts.

Most preferably, the *Bacillus* species that can be contained in the spore formulations can produce and/or be capable of producing one or more enzymes including, but not limited to, proteases, amylases, lipases, glycosidases, cellulases, esterases, and xylanases. Tests and assays for determining the production of such enzymes from a *Bacillus* species are generally known in the art and to one of ordinary skill in the art.

According to one preferred embodiment, the spore formulation can contain about 0.1% to 90% by weight spores, along with salt or other suitable carrier, such as sodium bicarbonate, or maltodextrin, or a combination thereof. In some embodiments, the spore formulation contains about 5% by weight spores. The spore formulation can be and/or include a powder or other dry form (e.g. spray-dried form of a liquid spore concentrate, or lyophilized spore formulation) containing spores. According to another preferred embodiment, the total concentration of spores in the spore formulation can range from about $1\times10^5$ CFU/mL or spores/g to $1\times10^{14}$ CFU/mL or spores/g or any specific concentration or range therein. The total preferred concentration of spores in the spore formulation can be about 1, 1.125, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, or $9.75\times10^5$, $10^6$, $10^7$, $10^8$, $10^9$, $10^{10}$, $10^{11}$, $10^{12}$, $10^{13}$, or $10^{14}$ CFU/mL or spores/g or any range or other value therein. According to another preferred embodiment, any one specific spore species can be present in the spore formulation at a concentration that can range from about $1\times10^5$ CFU/mL to $1\times10^{14}$ CFU/mL or any specific range therein. The preferred concentration of any one specific spore species present in the preferred embodiments of spore formulations according to the invention can be about 1, 1.125, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, or $9.75\times10^5$, $10^6$, $10^7$, $10^8$, $10^9$, $10^{10}$, $10^{11}$, $10^{12}$, $10^{13}$, or $10^{14}$ CFU/mL or spores/g or any range or other value therein. Preferably, the spore formulation is biodegradable. According to another preferred embodiment, the concentrated spore formulation can contain about $1-9\times10^9$ or $10^{10}$ CFU/mL or spores/g. According to another preferred embodiment, the concentrated spore formulation can contain about $10^{10}$ CFU/mL or spores/g.

According to one preferred embodiment of a probiotic tea composition, the composition comprises a nutrient composition, a spore formulation, and tea. According to another preferred embodiment or a probiotic composition for human consumption, the composition comprises a nutrient composition, a spore formulation, and a food or beverage product, such as soups, gravies, sauces, hot chocolate. Most preferably, the nutrient composition and spore formulation in these embodiments are one of the above described embodiments, both in dry powdered or other dry solid form. Any variety of tea or other food or beverage product may be used. Most preferably, the food or beverage product is one that is heated before being consumed.

According to one preferred method of providing probiotic tea for human consumption, a nutrient composition and spore formulation are added to any variety of tea. Most preferably, the nutrient composition and spore formulation are one of the above described embodiments. According to one preferred embodiment, the nutrient composition, spore formulation, and tea or other food or beverage product are combined into a mixture prior to steeping in hot water or otherwise heating the food or beverage product. The nutrient-germinant composition, one or more species of *Bacillus* spores, and a food or beverage product may be pre-mixed in any combination. According to one preferred embodiment, water is added to the mixture and the probiotic food or beverage composition is heated to a temperature range of 42 to 100° C. to germinate the probiotic spores prior to being consumed. According to another preferred embodiment, the probiotic food or beverage composition is heated to a temperature range of 44° C. to 60° C. According to other preferred embodiments, the nutrient composition, spore formulation, and tea may be separate components that are added together to hot water to prepare the probiotic tea or added to the other food or beverage product to be heated or already heated, or any combination of two of the components may be pre-mixed together and added to the third component prior to or after adding hot water to prepare the probiotic tea or prior to or after heating the other food or beverage product. The order of addition of the three components and the hot water or hot food or beverage is not critical and any order may be used. When used for tea, after mixing or adding the three components, individually or as a pre-mixed combination, with hot water, the mixture is allowed to steep, preferably for 2 to 10 minutes prior to being consumed by a human. Two minutes is the preferred minimum amount of steeping time, but the total time may vary based on the type of tea used and the strength of the tea desired by the person who will consume the probiotic tea. For example, green tea is typically steeped for 2-4 minutes while Oolong tea is typically steeped for 5-8 minutes. Consumption is preferably by drinking or otherwise orally ingesting the probiotic tea. Most preferably, the hot water is at a temperature in the range of 42 to 100° C. when initially added to the other components. The hot water temperature is preferably not below 42° C., and the range may vary based on the type of tea being used. For example, green tea is typically steeped in the range of 65-80° C. and black tea is usually steeped in the range of 80-100° C.

Various compositions according to preferred embodiments of the invention were tested according to preferred methods of the invention. The compositions, methods, and results are described below.

Example 1

A probiotic blend of *Bacillus* spores (*B. subtilis* and *B. licheniformis*) at a final concentration of approx. $4 \times 10^6$ CFU/mL, where CFU stands for colony forming unit, and a nutrient germinant composition according to a preferred embodiment of the invention comprising L-alanine (0.21 g), monosodium phosphate (0.14 g), and disodium phosphate (0.5 g), were added to approx. 8 fluid ounces of tap water at various temperatures.

The amount of spores added represents a "dose" of $10^9$ CFU of probiotic bacteria, as recommended by a Harvard Health study. The amount of nutrient germinants used represents the minimum concentration of germinants necessary to initiate germination. The temperatures used represent a range of tea steeping temperatures.

Spores from each reaction were observed at time 0 and after 60 minutes using phase contrast microscopy. Slides were prepared using standard procedures. Spores were viewed on an Olympus BX41 microscope (100× oil emersion objective) and imaged using an Olympus UC30 camera controlled by the cellSens Dimension software package.

FIG. 1 shows representative images from these tests at time 0 (i.e. immediately after water addition) and after 60 minutes in the water. The darker spots show germinated spores, the lighter spots show non-germinated spores. The images in group A represent spores that had been germinated using a nutrient-germinant composition and heated during the incubation period at 42° C. according to a preferred composition and preferred method of the invention. The images in group B represent spores that had been germinated using a nutrient-germinant composition and heated during the incubation period at 65° C. according to a preferred composition and preferred method of the invention. The images in group C represent spores that had been germinated using a nutrient-germinant composition and heated during the incubation period at 75° C. according to a preferred composition and preferred method of the invention. The images in group D represent spores that had been germinated using a nutrient-germinant composition and heated during the incubation period at 85° C. according to a preferred composition and preferred method of the invention. The images in group E represent represents spores that had been germinated using a nutrient-germinant composition and heated during the incubation period at 100° C. according to a preferred composition and preferred method of the invention.

Taken together, these images show that *Bacillus* spores are germinated in the compositions and conditions of preferred embodiments of the present invention.

Example 2

Figure 2:
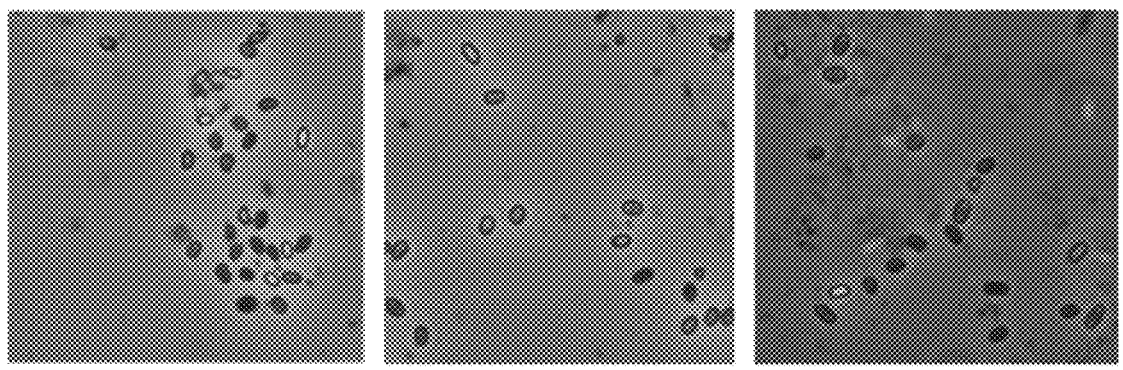
FIG. 2 shows photographs of *Bacillus* species and a nutrient germinant composition according to a preferred embodiment in steeped tea (black and green tea) according to a preferred method of the invention, the darker spots indicate germinated bacteria and the lighter/brighter spots indicate non-germinated spores.
Figure 2:
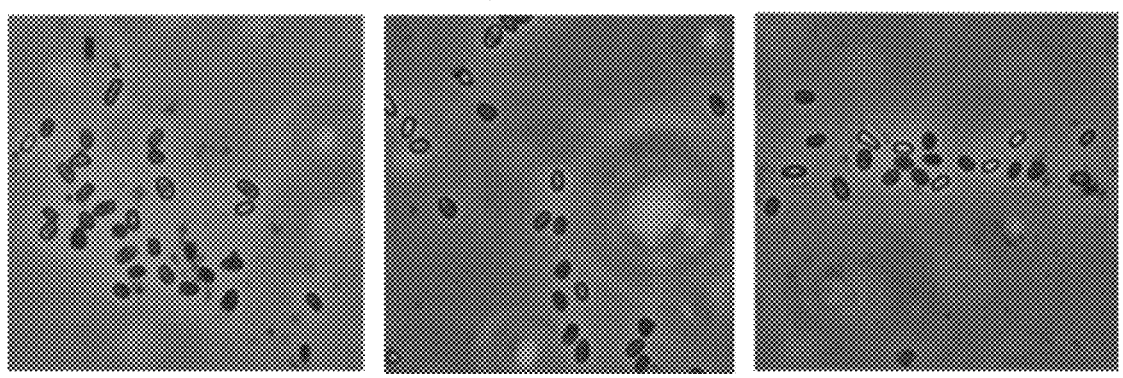

A probiotic blend of *Bacillus* spores (*B. subtilis* and *B. licheniformis*) at a final concentration of approx. $4 \times 10^6$ CFU/mL and a nutrient germinant composition, according to a preferred embodiment of the invention, comprising L-alanine (0.21 g), monosodium phosphate (0.14 g), and disodium phosphate (0.5 g), were added to approx. 8 fluid ounces of tap water at 85° C. A tea bag containing the indicated variety of tea (black or green as shown in FIG. 2) was steeped in the water for approx. 3 minutes, as recommended by the tea manufacturer. After steeping, the tea bags were removed while the spores remained in the mixture to be ingested as a probiotic dose.

Spores from each reaction were observed after 60 minutes using phase contrast microscopy. Slides were prepared using standard procedures. Spores were viewed on an Olympus BX41 microscope (100× oil emersion objective) and imaged using an Olympus UC30 camera controlled by the cellSens Dimension software package.

FIG. 2 shows representative images from these tests after 60 minutes in the water. The darker spots show germinated spores, the lighter/brighter spots show non-germinated spores. The top images represent spores germinated in steeped black tea (Lipton™) while the bottom images represent spores germinated in steeped green tea (Bigelow®).

Taken together, these images show that *Bacillus* spores are germinated in the compositions and conditions of preferred embodiments of the present invention and that compounds that are extracted from tea during steeping do not abate the germination process.

Although the above examples are in reference to use of probiotic compositions with tea, the compositions and methods of the invention may be used with other types of food or beverage products, such as soups, gravies, or hot chocolate. Most preferably, such food and beverage products are liquids or fluids and are consumed after heating, but other types of food and beverage products may also be used.

A nutrient-germinant composition according to one preferred embodiment of the invention comprises one or more L-amino acids, D-glucose (which increases the binding affinity of L-amino acids for their cognate receptors in the spore coat and is optional), D-Fructose (optional, depending on bacteria species), a biological buffer to provide the proper pH for spore germination (such as HEPES sodium salt, a phosphate buffer, or a Tris buffer), an optional source of potassium ions (such as KCl), and an industrial preservative. In another preferred embodiment, the composition comprises both D-glucose and D-fructose. It is most preferred to include a source of potassium ions, such as KCl, when both D-glucose and D-fructose are used. The use of D-fructose, a combination of D-glucose and D-fructose, and a potassium ion source are dependent on the species of bacteria as will be understood by those of ordinary skill in the art. It is preferred to use a preservative that is pH compatible with the composition, which has a relatively neutral pH. According to another preferred embodiment, the composition also comprises spores of one or more *Bacillus* species and one or more germination inhibitors. Alternatively, spores may be separately added to the nutrient-germinant composition according to the invention at the point-of-use. According to another preferred embodiment, the composition is in a concentrated form, most preferably as a concentrated liquid, and is diluted at the point-of-use.

Preferred L-amino acids include L-alanine, L-asparagine, L-valine, and L-cysteine. In a further embodiment of the concentrate composition, L-amino acids can be provided as a hydrolysate of soy protein. When in a concentrated form, the composition preferably comprises a solution of one or more of the above mentioned L-amino acids in the weight range of 8.9-133.5 g/L, more preferably 13.2-111.25 g/L, and most preferably 17.8-89 g/L each; D-glucose (optional) and/or D-fructose (optional) in the weight range of 18-54 g/L, more preferably 27-45 g/L, and most preferably 30-40 g/L each; KCl (optional, as a source of potassium) in the weight range of 7.4-22.2 g/L, more preferably 11.1-18.5 g/L, and most preferably 14-16 g/L; monosodium phosphate in a weight range of 10-36 g/L, more preferably 15-30 g/L, and most preferably 20-24 g/L; disodium phosphate in a weight range of 30-90 g/L, more preferably 21.3-75 g/L, and most preferably 28.4-60 g/L; and an one or more industrial preservatives at a final (total) weight range of 0.8-3.3 g/L, more preferably 1.2-2.7 g/L, most preferably 1.6-2.2. In addition to or in place of the monosodium/disodium phosphate buffer, the composition may comprise Tris base in a weight range of 15-61 g/L, more preferably 24-43 g/L, and most preferably 27-33 g/L; or HEPES buffer in a weight range of 32.5 97.5 g/L, more preferably 48.75-81.25 g/L, and most preferably 60-70 g/L. Optionally, monopotassium phosphate may also be used as a source of potassium ions, preferably in a weight range of 13.6-40.8 g/L, more preferably 20.4-34 g/L, and most preferably 26-29 g/L. Optionally, dipotassium phosphate may also be used as a source of potassium ions, preferably in a weight range of 8.7-26.1 g/L, more preferably 13-21.75 g/L, and most preferably 16-19 g/L. The amounts of these ingredients are important aspects of the invention because higher concentrations would render some ingredients insoluble and lower concentrations would be ineffective at germinating spores.

Most preferably, a nutrient-germinant concentrate composition according to embodiments of the invention is in concentrated form and is diluted to a working solution in water or any other appropriate diluent, preferably at the point-of-use. The dilution is preferably in a range from 0.1-10% of the concentrate and the balance water, but other amounts may also be used. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

According to one preferred embodiment, the composition preferably comprises 10% to 90% by weight of one or more *Bacillus* spores. The preferred *Bacillus* spores include the following species: *Bacillus licheniformis, Bacillus subtilis, Bacillus amyloliquiefaciens, Bacillus polymyxa, Bacillus thuringiensis, Bacillus megaterium Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex,* and *Bacillus sphaericus*. Other *Bacillus* spore species may also be used as will be understood by those of ordinary skill in the art. Most preferably, the composition comprises 3 to 12 *Bacillus* species. Alternatively, these spores may be separately added to the nutrient-germinant composition at the point-of-use.

In another preferred embodiment, a nutrient-germinant composition for use as a probiotic comprises one or more *Bacillus* strains that are probiotic in nature in that they aid in the breakdown of nutrients in the digestive tract of the consumer. The strains preferably produce one or more of the following enzymes: proteases to hydrolyze proteins, amylases to hydrolyze starches and other carbohydrates, lipases to hydrolyze fats, glycosidases to assist in the hydrolysis of glycosidic bonds in complex sugars and to assist in degradation of cellulose, cellulases to degrade cellulose to glucose, esterase which is a lipase-like enzyme, and xylanases that degrade xylan, a polysaccharide found in plant cell walls. *Bacillius* strains that produce these enzymes are well known in the art. Alternatively, these *Bacillus* strains may also be separately added to the nutrient-germinant composition at the point-of-use.

In another embodiment, a nutrient-germinant composition for use as a wastewater treatment or a drain treatment comprises one or more *Bacillus* strains that produce enzymes that are beneficial in the digestion of organic matter typically found in wastewater and/or drains. The *Bacillus* strains preferably produce one or more of the following enzymes: proteases to hydrolyze plant and animal proteins, amylases to hydrolyze starches and other carbohydrates, lipases to hydrolyze vegetable and animal fats, oils, and grease, glycosidases to assist in the hydrolysis of glycosidic bonds in complex sugars and to assist in degradation of cellulose, cellulases to degrade cellulose to glucose, esterase which is a lipase-like enzyme, and xylanases. Other enzymes may be produced, as well. The particular *Bacillus* species selected for inclusion in a preferred composition according to the invention may be one that specifically produces enzymes targeted for the particular type of organic matter that is found in the wastewater and/or drain being treated. *Bacillius* strains that produce these enzymes or are targeted for particular types of waste treatment are well known in the art. Again, as another alternative, these *Bacillus* strains may also be separately added to the nutrient-germinant composition at the point-of-use.

When spores are included in the nutrient-germinant composition, the composition also comprises one or more germination inhibitors and/or preservatives. Preferred germination inhibitors or preservatives include NaCl, D-alanine, or preservatives. Specifically, the composition comprises a high concentration of NaCl in the range of 29-117 g/L, more preferably 43-88 g/L, most preferably 52-71 g/L, and/or one or more chemical preservatives (such as Linguard ICP or Kathon CG (which has active ingredients comprising methyl chloro isothiazolinone, around 1.15-1.18% and methyl isothiazolinone, around 0.35-0.4%)) at a final (total) concentration of 0.8-3.3 g/L, more preferably 1.2-2.7 g/L, most preferably 1.6-2.2 g/L, and/or D-alanine (a known competitive inhibitor of germination) in the range of 8-116 g/L, more preferably 26-89 g/L, most preferably 40-50 g/L. These germination inhibitors or preservatives maintain the spores in an inactive state and prevent premature germination of the spores prior to their dilution and activation at the point-of-use. The use of germination inhibitors is particularly preferred when the composition according to this embodiment is used with the preferred method of the invention, where germination occurs at the point-of-use. The nutrient-germinant composition according to the invention optionally comprises other standard ingredients including, but not limited to, other preservatives that ensure the shelf-life of the composition and surfactants that aid in the dispersal of active ingredients, that are typically included in spore compositions or in industrial treatment products.

According to one preferred embodiment, a method of germinating spores at a point-of-use according to the invention comprises providing a composition comprising spores and nutrients (preferably a composition according to the invention, but the spores and nutrients may also be in separate compositions/separately added components) and heating the composition to an elevated temperature or range of temperatures and maintaining the composition at that temperature or within that range for a period of time (incubation period) to allow germination at a point-of-use location near a point-of-consumption. Heating during the incubation period takes place in the presence of the nutrient-germination composition in a single step. The method also preferably comprises the step of dispensing the germinated spores to an animal (through feed or water), animal bedding, plants, ponds, humans, wastewater system, or drain. Preferably, the spore composition is heated to a temperature in a range of 35-55° C., more preferably in the range of 38-50° C., and most preferably in the range of 41° C. to 44° C. The incubation period can vary depending on the end-use application. For a probiotic application, it is preferred that the incubation period lasts no longer than 10 minutes. Most preferably, in a probiotic application, the incubation period is between 2-5 minutes. In this way, spores are released to the animal before the spores have fully germinated and stand a better chance of surviving through to the animal's intestinal tract where they are most beneficial. On the other hand, a wastewater application may require a longer incubation period ranging between 20-60 minutes to ensure that fully germinated spores are delivered to the wastewater being treated. Most preferably, the incubation period is between 20-30 minutes for wastewater treatment. Regardless of application, the incubation may be in an air incubator, a water incubator, or any other chamber that provides even, constant heat at the given temperature range.

Various compositions according to preferred embodiments of the invention were tested according to preferred methods of the invention. The compositions, methods, and results are described below.

Example 3

To germinate spores, FreeFlow LF-88 Probiotic (spore liquid formula commercially available from NCH Corporation) was added to 1 mL of tap water at a final concentration of approx. $1 \times 10^9$ CFU/mL, where CFU stands for colony forming unit. A nutrient germinant concentrate composition according to a preferred embodiment of the invention comprising L-alanine (89 g/L), monosodium phosphate (20 g/L), disodium phosphate (60 g/L), and Linguard CP (1.6 g/L total) was added to the water and bacteria mixture to provide a 4% final concentration of nutrient-germinant composition by total weight of the mixture. For comparison, negative control reactions were prepared with the same amount of FreeFlow LF-88 Probiotic and water, but without adding the nutrient germinant concentrate composition. Both mixtures (germinant and negative control without the nutrient-germinant composition) were blended and incubated for 60 minutes in a pre-incubated heat block set to 42° C. or at ambient room temperature (around 23° C.).

Spores from each reaction were observed using phase contrast microscopy. Slides were prepared using standard procedures. Spores were viewed on an Olympus BX41 microscope (100× oil emersion objective) and imaged using an Olympus UC30 camera controlled by the cellSens Dimension software package.

Images were taken and germinated spores were counted as a percentage of the total spores in the field. A total of 10 representative images were analyzed for each condition (test mixture). Germinated spores lose their refractivity due to the influx of water and are phase-dark while non-germinated spores are phase-bright.

Figure 3:
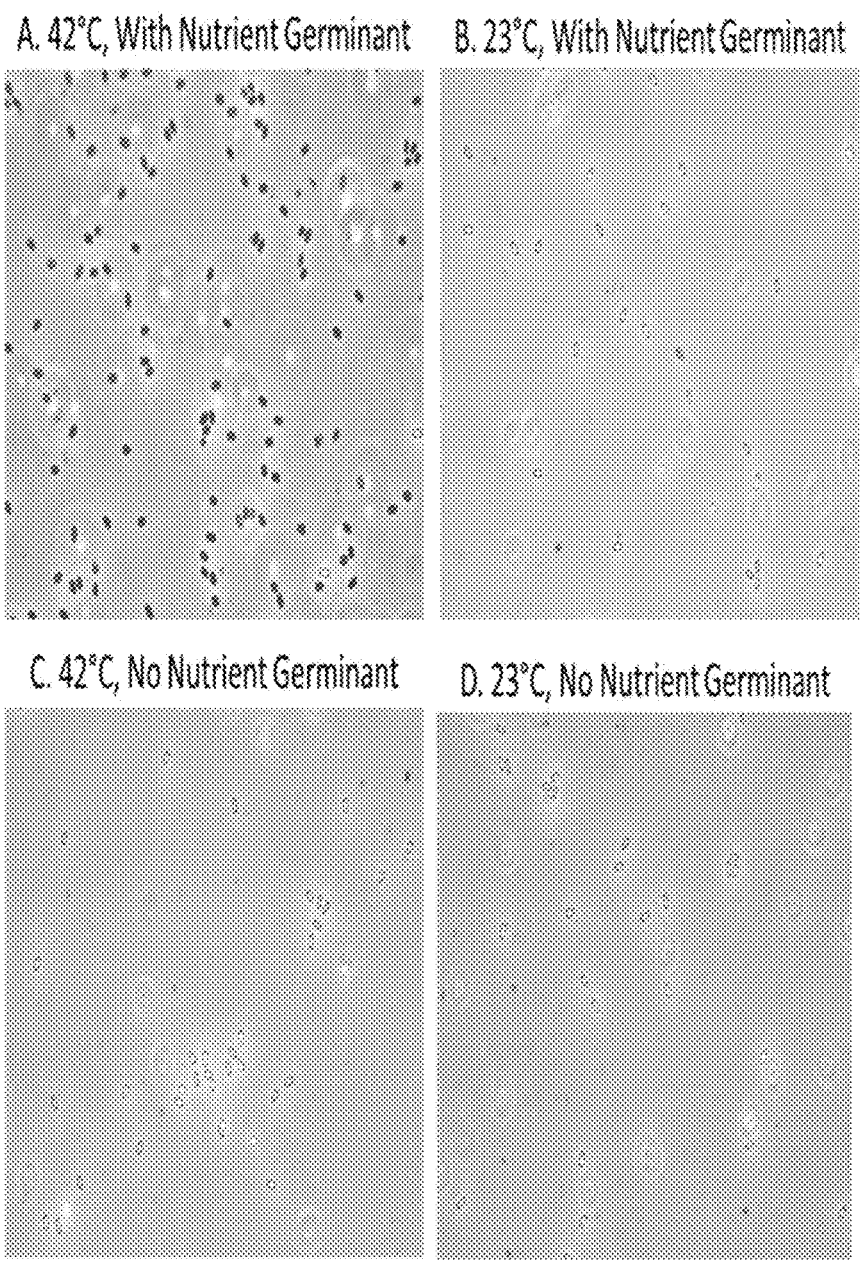
FIG. 3 shows photographs of bacteria slides using a composition and method according to a preferred embodiment of the invention compared to control slides.

FIG. 3 shows representative images from these tests. Image A represents spores that had been germinated using a nutrient-germinant composition and heated during the incubation period at 42° C. according to a preferred composition and preferred method of the invention. The darker spots show germinated spores, the lighter spots show non-germinated spores. Image B represents spores that had been germinated using a nutrient-germinant composition according to a preferred embodiment of the invention, but were incubated at ambient temperature (23° C.). Images C-D represent control spores that had not been treated with a nutrient germinant composition according to the invention, one having been incubated at 42° C. and one incubated at ambient temperature (23° C.).

As can be seen in FIG. 3, the "A" image shows significantly more germinated spores (dark spots) than the other images. Spores incubated with a nutrient-germinant composition according to a preferred embodiment invention in combination with a germination method according to a preferred embodiment of the invention show an apparent germination efficiency of 96.8% (Example 3, FIG. 3A). Control spores that had been incubated with a nutrient-germinant composition according to a preferred embodiment of the invention, but without using a germination method according to a preferred embodiment of the invention showed an apparent germination efficiency of 2.3% (Example 3, FIG. 3B). Similarly, spores that had not been incubated with a nutrient-germinant composition according to the invention showed an apparent activation efficiency of 1.2% and 2.6% at 42° C. and 23° C., respectively (Example 3, FIGS. 3C and 3D). Germinated spores in the samples not treated by preferred embodiments of the present method represent the small percentage of spores already germinated in the FreeFlow LF-88 Probiotic solution. This example demonstrates that spore germination is significantly increased when a nutrient-germinant composition and incubation method according to preferred embodiments of the invention are used together.

Example 4

Another set of incubation tests were run using the same test mixture/incubation method (using the same nutrient-germinant composition and heated incubation, "Treated Spores, 42° C.") and control mixture/incubation method (no nutrient-germinant composition and no heat, "Non-treated Spores, 23° C.") as described above in Example 1 were repeated, but different tests were run to compare the efficacy of the test mixture according to preferred embodiments of the invention as compared to the control mixture. Additionally, two other mixtures were tested—one in which the nutrient-germinant composition of Example 3 was used but without heat ("Treated Spores, 23° C.") and one in which no nutrient-germinant was used but the spores were heated ("Non-Treated Spores, 42° C."). Briefly, spores were incubated at 42° C. or 23° C. for 1 hour with or without treatment with a preferred nutrient-germinant composition. After incubation, the spores from 1 mL of each reaction were pelleted at 14K RPM for 3 min at 23° C. and resuspended in 1 mL of Butterfield's buffer. Approx. $6 \times 10^5$ CFUs (0.02 mL) were added to 0.980 mL of Davis minimal media (containing 3% glucose as a carbon source and trace elements) with an excess of D-alanine. D-alanine is a potent inhibitor of L-amino acid-mediated germination.

Approx. $1.2 \times 10^5$ CFUs were added to each of four wells of a PreSens OxoPlate. PreSens OxoPlates use optical oxygen sensors to fluorescently measure the oxygen content of the sample using two filter pairs (excitation: 540 nm, emission: 650 nm and excitation: 540, emission: 590 nm). Controls were performed as described by the manufacturer and measurements were taken on a BioTek 800FLx fluorescence plate reader. Time points were taken every 10 minutes for 24 hours at 37° C. with continual shaking and data was processed to determine the partial pressure of oxygen ($pO_2$) using the following formula:

$pO_2 = 100 * [(K_0/IR) - 1(K_0/K_{100}) - 1]$

Spores that have germinated and continue to divide and grow as vegetative cells consume oxygen as part of their metabolic growth. Oxygen consumption is represented by a drop in $pO_2$. Presumably, the growth that is observed is due to the outgrowth and vegetative growth of spores germinated by the present invention. The $pO_2$ levels for these tests are shown in FIG. 4.

Figure 4:
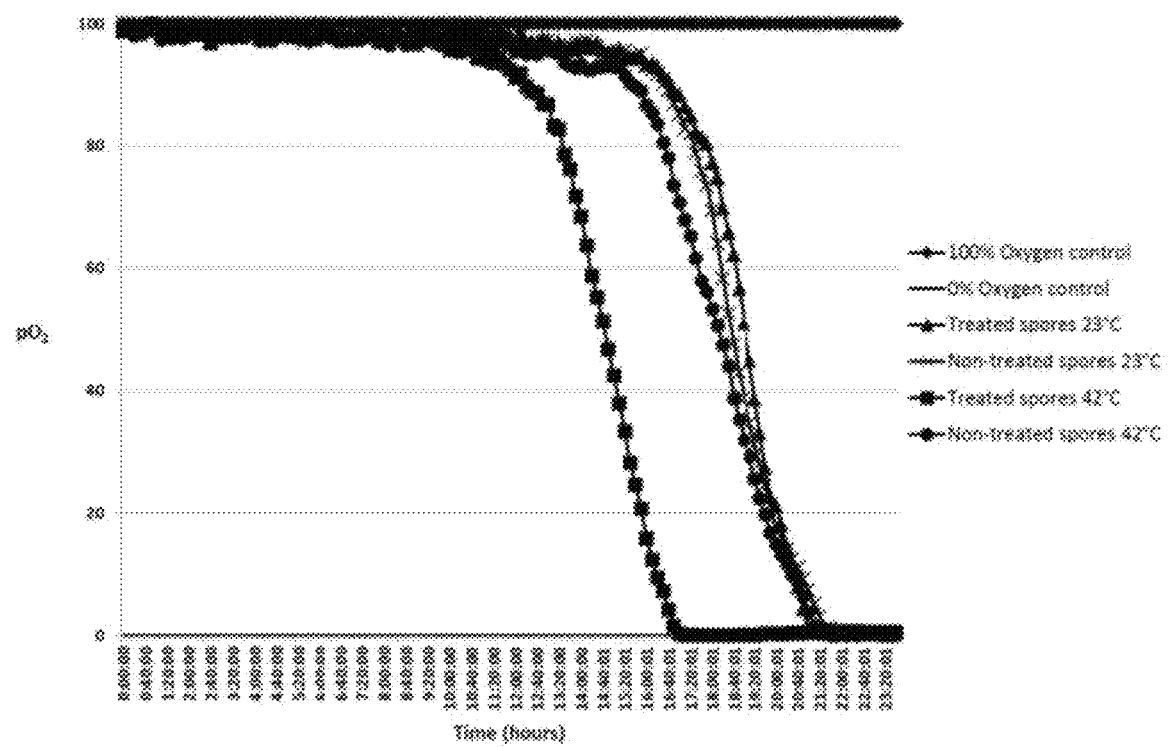
FIG. 4 is a graph showing $pO_2$ test data to demonstrate germination levels using a composition and method according to a preferred embodiment of the invention compared to control tests.

As shown in FIG. 4, incubation with the test mixture and method according to preferred embodiments of the invention (Treated spores 42° C., using both the nutrient-germinant composition and heating) resulted in spores that began vegetative growth 4 hours faster than the control spore mixtures that had not been treated or heated according to preferred embodiments of the invention or had been either treated with a nutrient-germinant composition or heated, but not both together. The growth seen in the control experiments presumably represents the approx. 2% of germinated spores present in FreeFlow LF-88 Probiotic (see EXAMPLE 3). This example further indicates that spore germination is significantly increased when a nutrient-germinant composition and incubation method according to preferred embodiments of the invention are used.

Example 5

Another set of incubation tests were run using a similar test and control mixture and incubation method as described above in Example 3. Briefly, LF-88 was added to 10 mLs of distilled water at a final concentration of approx. $10^8$ CFU/mL. Samples were incubated at various temperatures to show the efficacy of the test method according to preferred embodiments of the invention as compared to the control mixture. Reactions were prepared with the nutrient-germinant composition described in Example 3 ("Treated spores" in FIG. 3) and incubated at 23° C. (ambient temperature, no heating), 32° C., 42° C., or 60° C. A control reaction was incubated at ambient room temperature with no nutrient-germinant composition. After one hour of incubation, 1 mL of each reaction was pelleted at 14K RPM for 3 min at 23° C. and resuspended in Butterfield's buffer. Approx. $6 \times 10^5$ CFUs (0.02 mL) were added to 0.980 mL of Davis minimal media (containing 3% glucose as a carbon source and trace elements) with an excess of D-alanine.

Approx. $1.2 \times 10^5$ CFUs were added to each of four wells of a PreSens OxoPlate. Controls were performed as described by the manufacturer and measurements were taken on a BioTek 800FLx fluorescence plate reader using two filter pairs (excitation: 540 nm, emission: 650 nm and excitation: 540, emission: 590 nm). Time points were taken every 10 minutes for 24 hours at 37° C. with continual shaking and data was processed to determine the partial pressure of oxygen ($pO_2$). The $pO_2$ levels for these tests are shown in FIG. 5.

Figure 5:
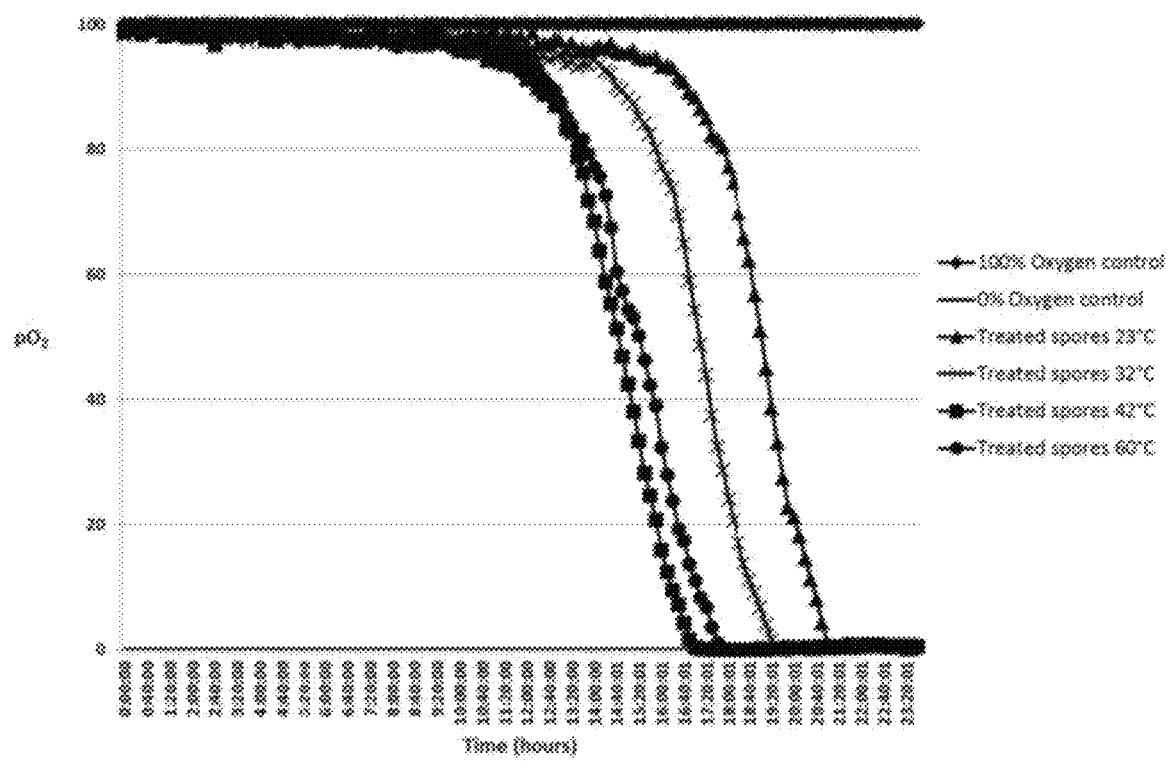
FIG. 5 is a graph showing $pO_2$ test data to demonstrate germination levels using a composition and varied methods according to preferred embodiments of the invention compared to control tests.

As shown in FIG. 5, incubation using a nutrient-germinant composition and heating according to preferred embodiments of the invention resulted in spores that began vegetative growth hours before the control. Spores treated with the nutrient-germinant composition but not heated are comparable to the control mixture. Spores treated with the nutrient-germinant composition that were incubated at a temperature below the preferred range of range of 35-55° C. according to one embodiment of the invention (represented by the "Treated spores 32° C." curve) begin vegetative growth faster than control experiments, but not as fast as spores treated at elevated temperatures within the preferred ranges according to the invention. Spores treated with a nutrient-germinant composition and incubated at a temperature within the most preferred range of 41° C. to 44° C. according to an embodiment of the invention showed the best results, being the first to begin vegetative growth and beginning growth 4 hours faster than the control. As seen in previous examples, growth seen in the no-treatment control experiment presumably represents the approx. 2% of germinated spores present in FreeFlow LF-88 Probiotic (see EXAMPLE 3). This example further indicates that spore germination is significantly increased when a nutrient-germinant composition and incubation method according to preferred embodiments of the invention are used.

All amounts for ingredients or ratios of ingredients indicated herein as a range include each individual amount or ratio within those ranges and any and all subset combinations within ranges, including subsets that overlap from one preferred range to a more preferred range. Those of ordinary skill in the art will appreciate upon reading this specification, including the examples contained herein, that modifications and alterations to the composition and methodology for making the composition may be made within the scope of the invention and it is intended that the scope of the invention disclosed herein be limited only by the broadest interpretation of the appended claims to which the inventor is legally entitled.

We claim:

1. A probiotic food or beverage composition for human consumption, the composition comprising:
    one or more *Bacillus* species in spore form;
    one or more L-amino acids;
    any variety of food or beverage product;
    one or more phosphate buffers to maintain the pH of the composition when added to water in a range of around 6-8;
    wherein the composition is heated to a temperature in a range of 42° C. to 100° C.;
    wherein the food or beverage product is any variety of tea, coffee, hot chocolate, soup, gravy, or sauce; and
    wherein all ingredients are GRAS (Generally Regarded as Safe) for human consumption under U.S. federal standards.

2. The probiotic food or beverage composition according to claim 1 wherein the one or more the L-amino acids is L-alanine, L-asparagine, L-valine, L-cysteine, a hydrolysate of soy protein, or a combination thereof.

3. The probiotic food or beverage composition according to claim 2 wherein the composition further comprises at least one of the following: (1) D-glucose, (2) D-fructose, (3) an osmoprotectant or (4) a source of potassium ions.

4. The probiotic food or beverage composition according to claim 1 wherein the composition further comprises at least two of the following: (1) D-glucose, (2) D-fructose, (3) an osmoprotectant and (4) a source of potassium ions.

5. The probiotic food or beverage composition according to claim 2 further comprising potassium chloride.

6. The probiotic food or beverage composition according to claim 2 wherein the *Bacillus* species are one or more of *Bacillus licheniformis, Bacillus subtillis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus pumilus, Bacillus simplex, Bacillus sphaericus, Bacillus sonorensis, Bacillus, horneckiae, Bacillus axarquiensis, Bacillus mucilaginosus, Bacillus olivae.*

7. The probiotic food or beverage composition according to claim 2 wherein the *Bacillus* species are *Bacillus licheniformis*, or *Bacillus subtilis*, or a combination thereof.

8. The probiotic food or beverage composition according to claim 7 wherein the *Bacillus* species are two different strains of *Bacillus licheniformis* and at least one strain of *Bacillus subtilis.*

9. The probiotic food or beverage composition according to claim 8 wherein the *Bacillus* species comprises around 40% of a first strain of *Bacillus licheniformis*, around 40% of a second strain of *Bacillus licheniformis*, and around 20% of the at least one strain of *Bacillus subtilis.*

10. The composition of claim 2 further comprising a source of potassium ions.

11. The probiotic food or beverage composition according to claim 1 wherein the composition further comprises an osmoprotectant.

12. The probiotic food or beverage composition according to claim 11 wherein the food or beverage product is a soup.

13. The probiotic food or beverage composition according to claim 11 wherein the food or beverage product is a gravy or sauce.

14. The probiotic food or beverage composition according to claim 7 wherein the composition further comprises an osmoprotectant.

15. The probiotic food or beverage composition according to claim 14 wherein the composition further comprises a source of potassium ions.

16. The probiotic food or beverage composition according to claim 8 wherein the composition further comprises an osmoprotectant.

17. The probiotic food or beverage composition according to claim 1 further comprising a preservative or germination inhibitor.

18. The probiotic food or beverage composition according to claim 17 wherein the preservative or germination inhibitor comprises propylparaben, methylparaben, NaCl, D-alanine, or a combination thereof.

19. The probiotic food or beverage composition according to claim 18 wherein the composition is heated to a temperature in a range of 44° C. to 60° C.

* * * * *